United States Patent [19]

LeVeen et al.

[11] 4,418,693
[45] Dec. 6, 1983

[54] VEIN AND TUBING PASSER SURGICAL INSTRUMENT

[76] Inventors: Eric G. LeVeen, 3-3 Woodlake Rd., Albany, N.Y. 12208; Robert F. LeVeen, 312 Lombard St. Philadelphia, Pa. 19147; Jeanette L. Rubricius, 321 Confederate Cir., Charleston, S.C. 29407

[21] Appl. No.: 215,047

[22] Filed: Dec. 10, 1980

[51] Int. Cl.³ ............................................. A61B 17/00
[52] U.S. Cl. .................................... 128/303 R; 3/1.4
[58] Field of Search ................... 128/335, 303 R, 347; 3/1.4

[56] References Cited

U.S. PATENT DOCUMENTS

| 2,788,787 | 4/1957 | Trace | 128/303 R |
| 3,185,155 | 5/1965 | Slaten et al. | 128/303 R |
| 3,683,926 | 8/1972 | Suzuki | 3/1.4 |
| 3,999,551 | 12/1976 | Spitz et al. | 128/303 R |
| 4,319,363 | 3/1982 | Ketharanathan | 3/1.4 |

FOREIGN PATENT DOCUMENTS 2815614 10/1978 Fed. Rep. of Germany ........... 3/1.4
700121 11/1979 U.S.S.R. .......................... 128/303 R Primary Examiner—Kyle L. Howell
Assistant Examiner—Max F. Hindenburg
Attorney, Agent, or Firm—Gipple & Hale

[57] ABSTRACT

An apparatus for vessel transfer comprising a tubular outer member and an inner slidable member one of which is rigid and the other of which is flexible. After the apparatus has been inserted in the body tissue, the rigid member is withdrawn from the body leaving the flexible member in place. A vein, prosthesis or elastomeric tubing attaching structure is secured to the end of the flexible member so that the flexible member can be used to pull said vein, prosthesis or elastomeric tubing through the body tissues to an elected distant site where the tip of the flexible member has been surgically exposed.

11 Claims, 10 Drawing Figures

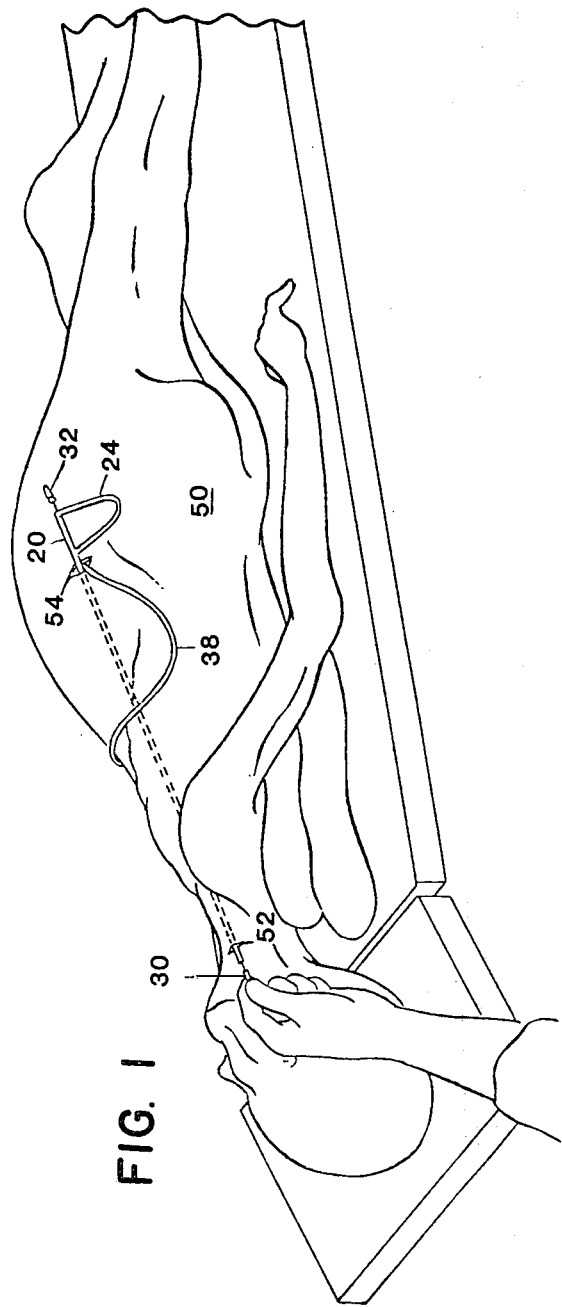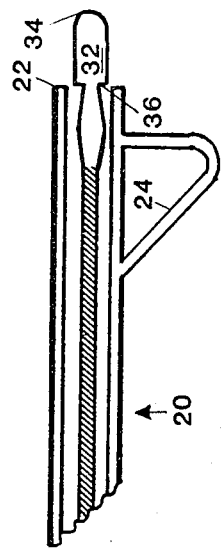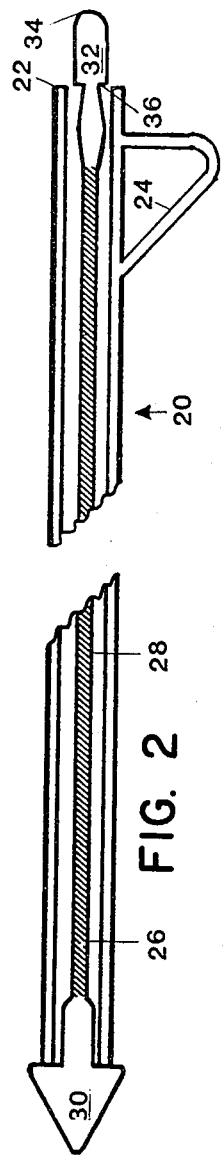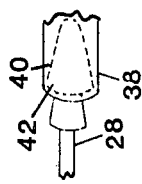

VEIN AND TUBING PASSER SURGICAL INSTRUMENT

DESCRIPTION OF THE PRIOR ART

The present invention generally relates to vascular surgery and more specifically to a tube passing apparatus.

In the performance of vascular surgery, it is frequently necessary to connect vessels with a tubular structure such as a section of saphenous vein or a segment of a prosthetic replacement for a natural vessel. Natural and synthetic material substrates are used to connect the femoral artery with the popliteal artery in cases where an arterial sclerotic occlusion is bypassed surgically to restore blood flow to the leg. These common surgical procedures are also often done in long incisions in the body of the patient or with the cumbersome passage of a heavy suture through the body to pull the tubing for the surgical procedure to a distant desired site.

It is sometimes necessary to extend elastomeric tubes from one place in the body to some distant site. Such a maneuver is done with a peritoneovenous shunt which requires that a tube connect the peritoneal cavity with a major vein in the chest cavity.

Other surgical procedures have used rigid tubular structures which are passed through the body. An artificial vessel is then drawn through the tubular structure. This procedure is very unsatisfactory since the tunnel made in the body tissue is much larger than need be made for the passage of the vessel or prosthesis. This enlarged tunnel or passageway makes it possible for blood or serum to accumulate around the path of the vessel or tubing exposing the patient to sepsis and fibrosis around the tract. Thus, it is extremely important that the tunnel should be no longer than the tubular structure to be passed.

One such example of the current state-of-the-art in the use of rigid tubular structures is disclosed in U.S. Pat. No. 3,866,609. In this reference, which is directed to the growing of a femoro-popliteal by-pass operation, a metal tunneling tube is inserted through an incision and forced through the leg tissues to occupy the position desired for the graft tube. A mandrel assembly comprising a flexible plastic rod with a plurality of layers consisting of an inner knitted coarse mesh fabric tube and an outer fine mesh fabric tube is inserted in the tunneling tube and the tunneling tube is withdrawn leaving the mandrel assembly in place in the leg. The incision is closed and the wound heals over. At a later date, the mandrel is withdrawn and the ends of the graft tube are connected to the intended natural tube or tubes.

The tunneling tube comprises a metal tube and contains a removable flexible core rod made of a suitable plastic such as TEFLON or LEXAN. The core rod which is of a smaller diameter than the tunneling tube has a rounded distal end portion which protrudes from the distal end of the tunneling tube. The distal end of the tunneling tube is slightly inturned to provide a snug sliding fit on the core rod which insures that the end of the tube will be completely closed by the core rod without leaving any opening between the tunneling tube and the core rod. The proximal end of the core rod is equipped with a tubular shaped handle portion which abuts the proximal end of the tunneling tube. The purpose of the core rod is to provide a plug for the distal end of the tunneling tube which is removable from the proximal end. As previously indicated the tunneling tube and core rod are forced down through the subcutaneous tissue of the leg to the required location at which point the core rod is withdrawn, leaving the tube in the leg. The tubular mandrel assembly is inserted into the tunneling tube and the tunneling tube is withdrawn leaving the tubular mandrel in place. At a later time the mandrel rod is withdrawn leaving the fabric tube in place. The reference also discloses the use of the tunneling tube in the connection of one artery with another artery.

SUMMARY OF THE INVENTION

The present invention is directed toward a surgical tubing passer comprising a hollow tubular member and an inner moveable member placed in the tube member. Both members are assembled as a single assembly which can be passed through the tissues of the body. While either of the two members can be flexible, the tubular member is preferably rigid and contains the flexible member. Once the rigid member has been inserted into the body to the desired location, the rigid tubular member is removed and the flexible inner member is used to pull a tissue substitute vessel or a tube through the tissues to a distant site which has been surgically exposed. The flexible inner member has a bullet-shaped tip secured to its distal end which fits snugly against the end of the rigid outer tube. This tip can be varied in diameter depending on the size of the passageway desired through the tissue. The flexible inner member traverses the length of the rigid tube and is longer than the rigid tube so that it extends beyond the length of the tube. The proximal end of the flexible member is integrally attached to a nipple member over which an elastomeric tubing can be engaged or a length of vein or plastic prosthesis tied. In actual practice, the assembly is passed through the tissues to a distal site of election where an incision has exposed the vessel to be joined. The bullet-shaped tip of the flexible member is grasped and held while the outer rigid tube is removed from the body leaving the flexible inner member in the tissue. A vessel, prosthesis or tube is attached to the nipple on the end of the flexible member and is drawn to the distant site of election where it is detached and joined to the exposed vessel. An alternate embodiment is also disclosed in which the inner member is rigid and the outer tubing is flexible.

These and other objects and advantages of the present invention will be more readily apparent in the following description when read in conjunction with the accompanying drawings, in which:

BRIEF DESCRIPTION OF THE DRAWINGS

FIG. 1 is a perspective view of a patient showing insertion of the venous tubing of a peritoneo-venous shunt from one incision in the abdomen to another incision in the neck where it will be joined to the jugular vein utilizing the inventive device.

FIG. 2 is a enlarged cross-sectional view of the invention device shown in FIG. 1;

FIG. 3 is a view of the incision shown in FIG. 1 with the outer rigid member removed and a tube or passage member about to be attached to the nipple end of the inner flexible member;

FIG. 4 is an enlarged view of the nipple end shown in FIG. 3 with the tubular passage member secured in place on the nipple;

DETAILED DESCRIPTION OF THE INVENTION

Figure 5:
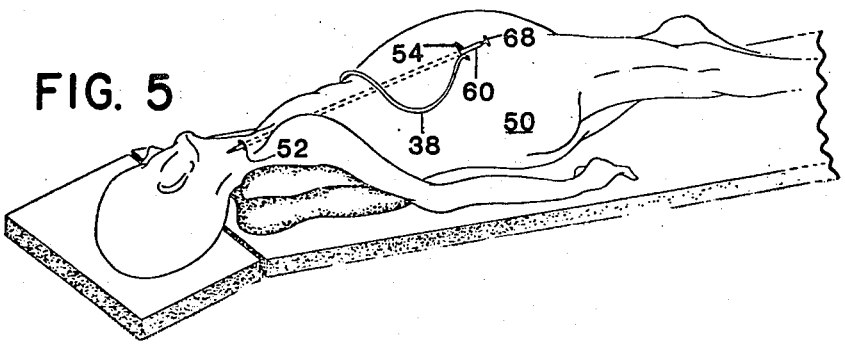
FIG. 5 is a perspective view of an alternate embodiment of the invention showing insertion of the device through respective incisions in the patient.
Figure 6:
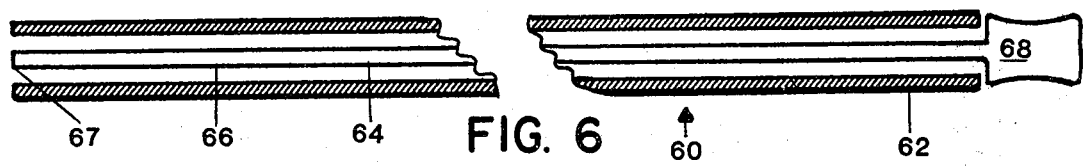
FIG. 6 is an enlarged cross-sectional view of the alternate embodiment shown in FIG. 5.

The present invention is shown by FIGS. 1 through 10 of the drawings. The preferred embodiment and best mode of the invention is shown in FIGS. 1 through 4. In the preferred embodiment and best mode of the invention, a tube pulling device 20 is disclosed having a rigid outer tubular member 22 with an integral extending triangular handle 24. Positioned within the tubular member 22 is a moveable inner member 26 comprising a flexible rod-shaped body 28 having an arrow or bullet shaped button 30 placed on its distal end and a nipple member 32 secured to is proximal end. The nipple member 32 has a rounded end 34 and shoulders 36 which are adapted to receive and hold a passing tube member 38. The nipple 32 can alternately be formed in a frusto-conical shape as shown in FIG. 4. The frusto-conically shaped member 40 is provided with shoulders 42 and is adapted to securely wedge into the artificial or natural vessel 38 so that the same can be pulled through the patient 50. The inventive tube pulling device 20 is utilized by making incisions 52 and 54 in a patient 50 and passing the device 20 through the incisions until the bullet-shaped end member 30 extends outside of incision 52 and the handle member 24 extends out of incision 54. The surgeon then grasps the bullet-shaped end member 30 firmly in one hand and pulls the rigid tubing 22 away from the bullet end member by means of handle 24 so that the entire outer tubing is pulled out of incision 54 leaving the flexible inner member 26 in place within the patient. The vessel 38 is forced over the nipple end member 32 so that it is firmly engages the nipple end by extending over shoulders 36 and the surgeon then pulls the flexible member 26 by means of bullet-shaped end member 30 out through the incision 52 drawing the vessel 38 behind the flexible member until the flexible member is pulled outside of incision 52 at which time the appropriate surgical connections can be made.

The alternate embodiment of the invention is shown in FIGS. 5 through 10. In this embodiment, the tube passing device 60 comprises a flexible outer tubing 62 with a moveable rigid inner member 64 comprising a rod section 66 and a stylet end 68. The passing device 60 is inserted into the patient in the same manner as passing device 20. However, the rigid member 64 is removed from the patient by pulling the stylet out through incision 54 leaving the flexible tubing within the patient with both ends of the flexible tubing extending out of the incisions 52 and 54 respectively. If desired, the distal end 67 of rod section 66 can be provided with a bullet-shaped end which has an outer diameter less than the inner diameter of flexible tubing 62.

Figure 7:
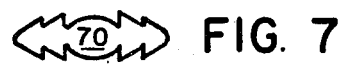
FIG. 7 is a cross-sectional view of a serrated connector which can be used as a connector member in the device shown in FIG. 6.
Figure 8:
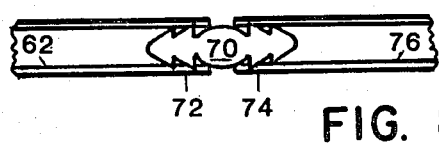
FIG. 8 is a cross-sectional view of the serrated connector shown in FIG. 7 showing the serrated connector member holding the flexible tubing.
Figure 9:
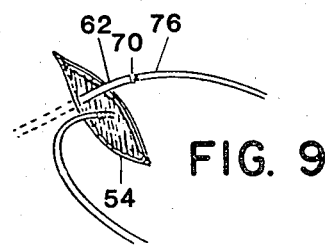
FIG. 9 is a perspective view of a connection as shown in FIG. 8 with the inner rigid member removed.
Figure 10:
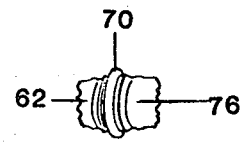
FIG. 10 is an enlarged perspective view of the connection made between the flexible outer tubing and the passage tubing.

A serrated connector 70 as shown in FIG. 7 is inserted into the proximal end 72 of the flexible tubing 62 and end 74 of the vessel 76 which is desired to be used in the operation so that both ends are securely fastened together. The flexible tubing is then pulled through incision 54 positioning the vessel 76 in the desired position in the patient so that respective ends of the tubing can be appropriately secured to the vessels in question for the desired surgical operation.

While the material composition of the invention has not been specified, it is understood that these materials are of acceptable biomedical composition which can be safely used in surgical procedures and meet accepted biomedical requirements. Thus, the rigid members can be of accepted materials such as surgical steel or rigid elastomers and the flexible materials can be flexible extruded elastomeric materials.

In the foregoing description, the invention has been described with reference to a particular preferred embodiment although it is to be understood that the details are merely illustrative and that the invention maybe carried out in other ways without departing from the true spirit and scope of the appended claims.

What is claimed is:

1. An apparatus for vessel transfer comprising a tubular outer member and an inner slidable member, one of which is rigid and one of which is flexible, said tubular outer member and inner slidable member being adapted to be passed through body tissue to an elected distant site which has been surgically exposed, a handle means extending aside and fixed to one end of said outer member, said handle means being adapted to insert said tubular outer member containing said inner slidable member into body tissue and to pull said tubular outer member from body tissue leaving said inner slidable member in body tissue, and attaching means adapted to attach a hollow vein, prosthesis or elastomeric tubing to one end of the flexible member after removing the outer member from the body tissue so that the flexible member can be used to pull said hollow vein, prosthesis or elastomeric tubing through the body tissue to said elected distant site, said attaching means comprising a body adapted to be inserted into said hollow vein, prosthesis or elastomeric tubing, said body having a diameter of at least a portion of its surface greater than the interior diameter of said hollow vein, prosthesis or elastomeric tubing.

2. Apparatus as claimed in claim 1 further comprising insertion means, wherein said outer member is in the form of a rigid tube, and said inner member is a flexible member having first and second ends with said insertion means secured on said first end, and said attaching means secured on said second end.

3. Apparatus as claimed in claim 2 wherein said attaching means is frusto-conical in shape.

4. Apparatus as claimed in claim 2 wherein said insertion means is a member having a diameter of at least a portion of its surface greater than the interior diameter of said tubular outer member.

5. Apparatus as claimed in claim 4 wherein said insertion means is arrow-shaped.

6. Apparatus as claimed in claim 4 wherein said insertion means is bullet-shaped.

7. A vessel transfer apparatus for transferring a hollow flexible conduit such as a blood vessel, prosthesis, elastomeric tubing or the like through body tissues comprising a rigid hollow tube member, handle means fixed to one end of said rigid hollow tube member, a flexible rod-like member moveably mounted within said rigid hollow tube member, said handle means being adapted to push said rigid hollow tube member and said rod-like member through body tissues and remove said rigid hollow tube member from body tissues, said flexible rod-like member comprising a rod-like body with attachment means on one end and a probe head on the other end, said attachment means defining an end surface adapted to be inserted in said hollow flexible conduit and shoulders adapted to engage and hold the interior of said hollow flexible conduit.

8. Apparatus as claimed in claim 7 wherein said probe head comprises an arrow-shaped head having its widest portion greater than the diameter of said hollow rigid tubular member.

9. Apparatus as claimed in claim 7 wherein said probe head comprises a bullet-shaped member having shoulders defined therein which extend past the diameter of said rigid tubular member.

10. Apparatus as claimed in claim 7 wherein said attachment means comprises a nipple-shaped end.

11. An apparatus for the transfer of a vessel within a human body comprising an assembly in a form of an outer tubular member and an inner slidable rod member positioned within said outer tubular member, one of said members being rigid and the other member being flexible, said rod member including means formed at one end which is of greater size than the interior diameter of said outer tubular member, handle means fixed to one end of said rigid member to push said assembly into body tissues and pull said rigid member from body tissues, said assembly being adapted to pass through body tissues to an elected distant site which has been surgically exposed so that the assembly is exposed, said flexible member being held within the body tissues while the rigid member of the assembly is removed from the body tissues, and attachment means to attach a hollow vein, prosthesis, elastomeric tubing or the like to an end of the flexible member after removal of the rigid member from the body tissues so that the flexible member can be used to lead said vein, prosthesis, elastomeric tubing or the like under tension through the body tissues to said elected distant site, said attachment means being adapted to engage and hold an interior surface of said vein, prosthesis, elastomeric tubing or the like.

* * * * *